United States Patent
Huh

(10) Patent No.: US 6,503,725 B2
(45) Date of Patent: Jan. 7, 2003

(54) COMPOSITION AND DEVICE FOR DETECTING LEUKOCYTES IN URINE

(75) Inventor: Nam-Won Huh, Eden Prairie, MN (US)

(73) Assignee: Hypoguard America Limited, Suffolk (GB)

( * ) Notice: Subject to any disclaimer, the term of this patent is extended or adjusted under 35 U.S.C. 154(b) by 0 days.

(21) Appl. No.: 10/024,887

(22) Filed: Dec. 18, 2001

(65) Prior Publication Data

US 2002/0058301 A1 May 16, 2002

Related U.S. Application Data

(62) Division of application No. 09/365,322, filed on Jul. 30, 1999, now Pat. No. 6,348,324
(60) Provisional application No. 60/116,613, filed on Jan. 21, 1999, and provisional application No. 60/143,383, filed on Jul. 12, 1999.

(51) Int. Cl.[7] .................. C12Q 1/44; C12Q 1/37; C07D 277/32
(52) U.S. Cl. .................. 435/19; 548/204; 548/187; 548/181; 546/270.4; 435/4; 435/23; 435/805; 424/9.1
(58) Field of Search .................. 435/19, 23, 805, 435/4; 424/9.1; 548/181, 204, 187; 546/270.4

(56) References Cited

U.S. PATENT DOCUMENTS

| | | |
|---|---|---|
| 3,552,928 A | 1/1971 | Fetter |
| 4,257,940 A | 3/1981 | Fujii et al. |
| 4,278,763 A | 7/1981 | Berger et al. |
| 4,296,202 A | 10/1981 | Berger et al. |
| 4,299,917 A | 11/1981 | Berger et al. |
| 4,428,874 A | 1/1984 | Svendsen |
| 4,442,033 A | 4/1984 | Berger et al. |
| 4,457,866 A | 7/1984 | Karges et al. |
| 4,499,185 A | 2/1985 | Skjold et al. |
| 4,517,301 A | 5/1985 | Greene |
| 4,529,704 A | 7/1985 | Trimmer et al. |
| 4,532,216 A | 7/1985 | Wang |
| 4,540,520 A | 9/1985 | Charlton et al. |
| 4,543,335 A | 9/1985 | Sommer et al. |
| 4,547,564 A | 10/1985 | Mark et al. |
| 4,551,428 A | 11/1985 | Berger et al. |
| 4,552,697 A | 11/1985 | Yip et al. |
| 4,616,053 A | 10/1986 | Schultz et al. |
| 4,637,979 A | 1/1987 | Skjold et al. |
| 4,645,842 A | 2/1987 | Corey |
| 4,657,855 A | 4/1987 | Corey et al. |
| 4,704,460 A | 11/1987 | Corey |
| 4,716,236 A | 12/1987 | Ward et al. |
| 4,723,020 A | 2/1988 | Hugl et al. |
| 4,749,648 A | 6/1988 | Berger et al. |
| 4,755,462 A | 7/1988 | Schnabel |
| 4,758,508 A | 7/1988 | Schnabel et al. |
| 4,772,553 A | 9/1988 | Fujii et al. |
| 4,774,340 A | 9/1988 | Corey et al. |
| 4,806,423 A | 2/1989 | Hugl et al. |
| 4,814,271 A | 3/1989 | Hugl et al. |
| 4,881,970 A | 11/1989 | Nagano et al. |
| 4,894,381 A | 1/1990 | Schade et al. |
| 5,015,572 A | 5/1991 | Backhaus et al. |
| RE34,284 E | 6/1993 | Matta et al. |
| 5,220,029 A | 6/1993 | Matta et al. |
| 5,270,281 A | 12/1993 | Otsuji et al. |
| 5,316,906 A | 5/1994 | Haugland et al. |
| 5,342,851 A | 8/1994 | Sanfilippo et al. |
| 5,391,806 A | 2/1995 | Otsuji et al. |
| 5,401,840 A | 3/1995 | Brion et al. |
| 5,424,215 A | 6/1995 | Albarella et al. |
| 5,424,440 A | 6/1995 | Klem et al. |
| 5,443,986 A | 8/1995 | Haughland et al. |

(List continued on next page.)

FOREIGN PATENT DOCUMENTS

| | | |
|---|---|---|
| EP | 0 158 226 B1 | 1/1991 |
| EP | 0 157 327 B1 | 6/1991 |
| GB | 1164530 | 9/1969 |
| JP | 7242639 | 9/1995 |
| SU | 1399661 | 5/1988 |

OTHER PUBLICATIONS

Chladek, S., "Aminoacyl Derivatives of Nucleosides, Nucleotides, and Polynucleotides. XIV. A General Synthesis of Adenosine 2'(3')–O–Peptidyl Derivatives", *J. Org. Chem.*, vol. 37, No. 18, pp. 2863–2867 (1972).

(List continued on next page.)

*Primary Examiner*—Charanjit S. Aulakh
(74) *Attorney, Agent, or Firm*—Merchant & Gould P.C.

(57) ABSTRACT

Thiazole esters are suitable for detecting the presence of leukocytes in urine. Such thiazole esters are suitable for use in compositions, diagnostic devices, and methods for detecting the presence of leukocytes. In one embodiment, a thiazole ester is of the formula:

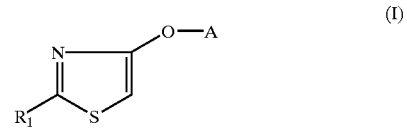

or a salt or solvated salt thereof, in which

A is an N-blocked amino acid residue or an N-blocked peptide chain, preferably N-blocked alanine or N-blocked polyalanine; and $R_1$ is unsubstituted or substituted heteroaryl; alkenyl substituted with unsubstituted or substituted aryl; or alkenyl substituted with unsubstituted or substituted heteroaryl. For example, $R_1$ may be thienyl, pyridyl, furyl, styryl, pyrrolyl, or indolyl. In still another embodiment, the thiazole ester includes unsubstituted or substituted fused hydrocarbyl rings as a substituent. In one embodiment, fused hydrocarbyl rings include naphthyl. In another embodiment, fused hydrocarbyl rings include anthryl.

62 Claims, No Drawings

U.S. PATENT DOCUMENTS

| | | | |
|---|---|---|---|
| 5,464,739 | A | 11/1995 | Johnson et al. |
| 5,475,122 | A | 12/1995 | Hoenel et al. |
| 5,502,182 | A | 3/1996 | Brion et al. |
| 5,512,450 | A | 4/1996 | Johnson et al. |
| 5,556,962 | A | 9/1996 | Brion et al. |
| 5,585,247 | A | 12/1996 | Habenstein |
| 5,614,520 | A | 3/1997 | Kondo et al. |
| 5,643,929 | A | 7/1997 | Diana et al. |
| 5,648,229 | A | 7/1997 | Habenstein |
| 5,663,044 | A | 9/1997 | Noffsinger et al. |
| 5,696,001 | A | 12/1997 | Habenstein |
| 5,750,359 | A | 5/1998 | Huh et al. |
| 5,846,754 | A | 12/1998 | Pugia et al. |
| 5,883,287 | A | 3/1999 | Akhavan-Tafti et al. |

OTHER PUBLICATIONS

Gut, V. et al., "Aminoacyl Derivatives of Nucleosides, Nucleotides, and Polynucleotides. XI. The Use of 5–Chloro–8–Hydroxyquinoline (Chloroxine) Esters in the Selective Acylation of Nucleoside and Oligonucleotide Aminoacyl Derivatives", *Collection Czechoslov. Chem. Commun.*, vol. 35, pp. 2398–2407 (1970).

Holt, S. et al., "The Importance of Osmiophilia in the Production of Stable Azoindoxyl Complexes of High Contrast for Combined Enzyme Cytochemistry and Electron Microscopy", *J. Cell Biol.*, vol. 29, pp. 361–366 (1966).

Jones, J. H. et al., "Amino–acids and Peptides. Part XXVIII. Anchimeric Acceleration of the Aminolysis of Esters. The Use of Mono–esters of Catechol in Peptide Synthesis", *J. Chem. Soc.* pp. 436–441 (1968).

Lapatsanis, L. et al., "Synthesis of Some Steroidal Esters of α–Amino Acids", *J. Chem. Eng. Data*, vol. 25, pp. 287–289 (1980).

Mukaiyama, T. et al., "A New Method for the Preparation of Active Esters of Various Amino Acids by Oxidation–Reduction Condensation", *Tetranearon Letters*, No. 60, pp. 5293–5296 (1970).

Pendergrass, J. et al., "A Control System for Monitoring the Performance of Leukocyte Strip Tests," *Clin. Chem.*, vol. 32, No. 7, pp. 1400–1402 (1986).

Yajima, H. et al., "Studies on Peptides. XLVIII. Application of the Trifluoromethanesulphonic Acid Procedure to the Synthesis of Tuftsin", *Chem. Pharm. Bull.*, No. 2, pp. 371–374 (1975).

COMPOSITION AND DEVICE FOR DETECTING LEUKOCYTES IN URINE

This application is a divisional of application Ser. No. 09/365,322, filed Jul. 30, 1999, now U.S. Pat. No. 6,348.324, which claims priority from Provisional Application Ser. No. 60/116,613, filed Jan. 21, 1999 and Provisional Application Ser. No. 60/143,383, filed Jul. 12, 1999, which application(s) are incorporated herein by reference.

FIELD OF THE INVENTION

This invention relates generally to compounds, compositions, devices, and methods useful for detecting the presence of leukocytes through the activity of leukocyte esterases and proteinases in urine.

BACKGROUND OF THE INVENTION

The presence of leukocytes in human urine is associated with infection or malfunction in the kidney or urinary tract. Accurate detection has a significant meaning for the physiological treatment or diagnosis of the patient.

A basic method to measure the number of leukocytes in urine by microscope has been widely available for some time. However, the disadvantages of this method include the investment of time and money in obtaining and installing the appropriate instrumentation. Further, false negatives can be obtained when samples are allowed to sit too long before analysis.

Research has been directed to developing other methods, such as indicator assays, that are suitable for detecting leukocytes more easily, conveniently, and accurately. Typical indicator assays use a specific chemical substance (e.g., a substrate) that is degraded by one or more enzymes present in leukocytes to create a product suitable for effectuating a visible color change.

One such leukocyte assay is disclosed in U.S. Pat. No. 3,087,794 and involves the use of peroxidase that is contained in a granular leukocyte. This assay includes a filter paper stained with hydrogen peroxide and o-tolidine, which shows a colored oxidative product when contacted with leukocytes. Yet this assay is less than desirable because peroxidase can be dangerous and reductive materials in urine may make actual application impractical.

Other methods designed to confirm the presence of esterase and proteinase in leukocytes have also been developed. For example, one method uses a colorless or pale-colored ester compound as a substrate that is degraded by esterase into a colorless acid moiety and an alcoholic moiety. Then, under diazonium or oxidative reaction, the alcoholic moiety is converted to a second densely colored product. This method was derived from a process in which enzymatic degradation of the substrate naphtol-AS-D chloroacetate produced chloroacetate and naphtol-AS. Reaction of the naphtol-AS product with a diazonium salt resulted in the formation of a colored azo compound.

This assay allows for the determination of leukocyte concentration by the naked eye. Yet the use of this assay is less than desirable because the diazonium salt may react with urobilinogen or bilirubin contained in urine. As a result, concentrations of leukocytes greater than 500 cells/$\mu$l are often necessary to avoid a false-negative reading.

U.K. Patent No. 1,128,371 discloses other possible substrates, i.e., colorless indoxyl or thioindoxylesters. These substrates are degraded into indoxyl or thioindoxyl by esterase. Colored indigo or thioindigo may then be produced by reaction with oxygen in the air or by an oxidizer. Yet the use of an assay with these substrates is less than desirable because this is not sensitive and fails to detect leukocytes at a concentration less than 10,000 cells/$\mu$l.

Similarly, U.S. Pat. No. 4,278,763 suggests indoxyl-type substrates by disclosing a method of using indoxyl or thioindoxylamino acid ester as a substrate.

Other assays using pyrrole derivatives as substrates have also been disclosed. For example, U.S. Pat. No. 4,704,460 discloses use of an amino acid ester of a pyrrole derivative as a substrate. When this derivative is degraded in the presence of diazonium salt, a change in sample color to deep violet results. Moreover, the addition of a nucleophilic alcohol, such as decanol, greatly facilitates reaction rate, and in turn, allows detection of leukocyte concentrations as low as 10 cells/$\mu$l within 90 seconds. Yet this assay is less than desirable because the syntheses of these two substrates is very difficult.

The above-described assays are characterized by numerous disadvantages. Some disadvantages include the detection of false negatives, the interference of urobilinogen or bilirubin, the lack of sensitivity, and the requirement of less-than-desirable substrates. Thus, it would be desirable to identify new compounds and methods of using the compounds to detect the presence of leukocytes in urine.

SUMMARY OF THE INVENTION

The invention is directed to thiazole esters suitable for detecting leukocytes in urine, compositions containing thiazole esters, diagnostic devices suitable for detecting leukocytes in urine, and methods of using the thiazole esters or compositions thereof for detecting leukocytes in urine.

In one aspect, this invention is directed to novel thiazole esters.

One thiazole ester according to this invention is of the formula:

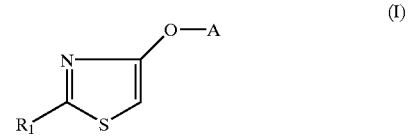

or a salt or solvated salt thereof, in which

A is an N-blocked amino acid residue or an N-blocked peptide chain, preferably N-blocked alanine or N-blocked polyalanine; and $R_1$ is unsubstituted or substituted heteroaryl; alkenyl substituted with unsubstituted or substituted aryl; or alkenyl substituted with unsubstituted or substituted heteroaryl. For example, $R_1$ may be thienyl, pyridyl, furyl, styryl, pyrrolyl, or indolyl.

Another thiazole ester according to this invention is of the formula:

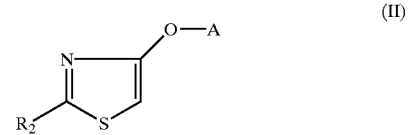

or a salt or solvated salt thereof, in which

A is an N-blocked amino acid residue or an N-blocked peptide chain, preferably N-blocked alanine or N-blocked polyalanine; and $R_2$ is unsubstituted or substituted fused hydrocarbyl rings in which at least one ring is aromatic. For example, $R_2$ may be naphthyl or anthryl.

In another aspect, this invention is directed to compositions that include a thiazole ester of formula I or II. Compositions of the invention may also include a diazonium salt such as 2-methoxy-4-morpholinobenzene diazonium chloride, zinc chloride double salt.

In still another aspect, this invention is directed to diagnostic devices that include a compound or composition of the invention. Such diagnostic devices include a substrate having a thiazole ester of formula I or II deposited thereon.

The compounds, compositions, and diagnostic devices of the invention are also suitable for use in methods for detecting leukocytes in urine. Methods for detecting leukocytes in urine include contacting a thiazole ester of the invention and a diazonium salt with a urine sample.

The compounds and compositions suitable for use in devices and methods of the invention are typically pharmaceutically acceptable.

DETAILED DESCRIPTION OF THE INVENTION

The invention is directed to detecting leukocytes in urine. The presence of leukocytes is typically detected by detecting the presence of enzymes known in the art as leukocyte esterases and leukocyte proteinases that are present with leukocytes.

Compounds of the invention include thiazole esters that contain an ester functionality, which is hydrolyzed upon exposure to leukocytes in urine. The hydrolysis of the ester of a thiazole ester of the invention provides a useful diagnostic technique because thiazolyl can react with a diazonium salt to produce an azo dye.

The compounds according to this invention are thiazole esters that are suitable for use in compositions, diagnostic devices, and methods that can be used to detect leukocytes in urine.

One thiazole ester suitable for use in compositions and methods of the invention is of the formula:

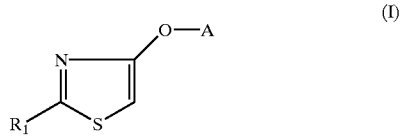

(I)

or a salt or solvated salt thereof, in which A is an N-blocked amino acid residue or an N-blocked peptide chain, preferably N-blocked alanine or N-blocked polyalanine (e.g., alanine-alanine, alanine-alanine-alanine, and the like), being blocked at the amino terminus by protecting groups known in the art, such as, for example, benzyloxycarbonyl, t-butoxycarbonyl, and p-toluenesulfonyl; and $R_1$ is unsubstituted or substituted heteroaryl; alkenyl substituted with unsubstituted or substituted aryl; or alkenyl substituted with unsubstituted or substituted heteroaryl.

The term "heteroaryl" includes heterocyclic aromatic derivatives having at least one heteroatom, such as, for example, nitrogen, oxygen, phosphorus, or sulfur, and includes, for example, furyl, pyrrolyl, thienyl, oxazolyl, pyridyl, imidazolyl, thiazolyl, isoxazolyl, pyrazolyl, isothiazolyl, and the like. The term "heteroaryl" also includes fused rings in which at least one ring is aromatic, such as, for example, indolyl, purinyl, benzofuryl, benzothienyl, quinolyl, 4,5,6,7-tetrahydro-1H-indolyl, and the like. In the case of fused rings that have a hydrocarbyl ring fused to a heterocyclic ring, such as, for example, benzothienyl and indolyl, the fused rings may be bonded to thiazolyl through either the hydrocarbyl ring or the heterocyclic ring. In some embodiments, heteroaryl includes a 5-membered ring. In other embodiments, heteroaryl includes a 6-membered ring.

Such heteroaryl groups may be unsubstituted or substituted on the ring by, for example, aryl, heteroaryl, alkyl, alkenyl, alkoxy, amino, acyl, halo, nitro, cyano, —$SO_3H$, or hydroxy, in which such substituents may further be substituted by aryl, heteroaryl, alkyl, alkenyl, alkoxy, amino, acyl, halo, nitro, cyano, —$SO_3H$, or hydroxy. In some embodiments, heteroaryl is substituted with alkyl, such as methyl, ethyl, propyl, or butyl. In other embodiments, heteroaryl is substituted with alkoxy, such as methoxy, ethoxy, propoxy, or butoxy. In still other embodiments, heteroaryl is substituted with aryl or heteroaryl.

The term "aryl" includes aromatic hydrocarbyl, such as, for example, phenyl, including fused aromatic rings, such as, for example, naphthyl.

The term "alkyl" includes a straight or branched saturated aliphatic hydrocarbon chain having from 1 to 4 carbon atoms, such as, for example, methyl, ethyl, propyl, isopropyl (1-methylethyl), butyl, t-butyl (1,1-dimethylethyl), and the like.

The term "alkenyl" includes an unsaturated aliphatic hydrocarbon chain having from 2 to 4 carbon atoms, such as, for example, ethenyl, 1-propenyl, 2-propenyl, 1-butenyl, 2-methyl-1-propenyl, and the like.

The above alkyl or alkenyl groups may optionally be interrupted in the chain by a heteroatom, such as, for example, a nitrogen or oxygen atom, forming an alkylaminoalkyl or alkoxyalkyl group, for example, methylaminoethyl or methoxymethyl, and the like.

The term "alkoxy" includes alkyl as defined above joined to an oxygen atom having from 1 to 4 carbon atoms in a straight or branched chain, such as, for example, methoxy, ethoxy, propoxy, isopropoxy (1-methylethoxy), butoxy, t-butoxy (1,1-dimethylethoxy), and the like.

The term "amino" includes a substituent of the formula —$N(R_3)_2$ in which each $R_3$ is independently hydrogen or alkyl. The term "alkyl" is as defined above.

The term "alkenyl substituted with unsubstituted or unsubstituted aryl" or "alkenyl substituted with unsubstituted or substituted heteroaryl" includes alkenyl as defined above, and such groups are substituted with unsubstituted or substituted aryl or unsubstituted or substituted heteroaryl, respectively. The terms "aryl" and "heteroaryl" are as defined above. Examples of suitable substituted alkenyls include styryl, cinnamyl, furylethenyl, pyridylethenyl, and thienylpropenyl.

In some embodiments, alkenyl substituted with unsubstituted or substituted aryl is alkenyl substituted with unsubstituted or substituted phenyl. This phenyl, in some embodiments, is substituted with alkoxy, such as methoxy, ethoxy, propoxy, or butoxy. In other embodiments, alkenyl substituted with unsubstituted or substituted heteroaryl is alkenyl substituted with a nitrogen-containing ring, oxygen-containing ring, or sulfur-containing ring.

Examples of $R_1$ groups for thiazole esters suitable for use in compositions and methods of the invention include 2-thienyl; 4-pyridyl; 2-furyl; β-styryl; 1,2-dimethyl-4-pyrrolyl; and 3-indolyl. It should be appreciated that one skilled in the art, having read this specification, would understand that a heteroatom may be at any one of several positions in a ring.

Another thiazole ester suitable for use in compositions and methods of the invention is of the formula

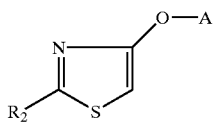
(II)

or a salt or solvated salt thereof, in which A is an N-blocked amino acid residue or an N-blocked peptide chain, preferably N-blocked alanine or N-blocked polyalanine (e.g., alanine-alanine, alanine-alanine-alanine, and the like), being blocked at the amino terminus by protecting groups known in the art, such as, for example, benzyloxycarbonyl, t-butoxycarbonyl, and p-toluenesulfonyl; and $R_2$ is unsubstituted or substituted fused hydrocarbyl rings in which at least one ring is aromatic.

Fused hydrocarbyl rings include at least two hydrocarbyl rings that maintain at least one bond in common between the rings, for example, naphthyl, anthryl, 5,6,7,8-tetrahydronaphthyl, phenanthrenyl, triphenylenyl, 1H-fluorenyl, and the like. Fused hydrocarbyl rings may be substituted by, for example, aryl, heteroaryl, alkyl, alkenyl, alkoxy, amino, acyl, halo, nitro, cyano, —$SO_3H$, or hydroxy, in which such substituents may further be substituted by aryl, heteroaryl, alkyl, alkenyl, alkoxy, amino, acyl, halo, nitro, cyano, —$SO_3H$, or hydroxy. These substituents are as defined above.

In some embodiments, fused hydrocarbyl rings contain at least one 5-membered ring. In other embodiments, fused hydrocarbyl rings contain at least one 6-membered ring. In still some embodiments, fused hydrocarbyl rings are substituted on at least one ring with alkyl, such as methyl, ethyl, propyl, or butyl. In other embodiments, fused hydrocarbyl rings are substituted on at least one ring with alkoxy, such as methoxy, ethoxy, propoxy, or butoxy.

In one embodiment, $R_2$ is 1-naphthyl.

A composition of the invention includes a thiazole ester of formula I or II. Such a composition may also include a diazonium salt such as 2-methoxy-4-morpholinobenzene diazonium chloride, zinc chloride double salt.

Compositions of the invention may be free of salts known in the art to have an accelerating action. Examples of salts that give an accelerating action include salts of monovalent and divalent cations of the alkali metals and alkaline earth metals, such as, for example, $Li^+$, $Na^+$, $K^+$, and $Mg^{++}$ as well as their typical anions.

A diagnostic device suitable for detecting leukocytes in urine includes a substrate suitable for supporting a thiazole ester of the invention, such as, for example, filter paper, filtration membrane, and other inert carriers. These substrates are known in the art. The diagnostic device also includes one or more thiazole esters of formula I or II. This compound is included with the substrate by, for example, sedimenting the derivative onto the substrate.

Generally, a novel diagnostic device may be prepared by combining the thiazole ester, an accelerator, and a diazonium salt. Accelerators suitable for use in compositions and methods of the invention are known in the art and include, for example, octanediol and decanol.

Diazonium salts suitable for use in compositions and methods of the invention are known in the art and include compounds that may be used for color-developing technology, such as, for example, 1-diazo-8-naphtol-3,6-disulfonic acid, chloride, zinc chloride double salt; 6-diazo-1-naphtol-3-sulfonic acid, chloride double salt; and 2-methoxy-4-morpholinobenzene diazonium chloride, zinc chloride double salt. Preferably, the diazonium salt used in accordance with the invention has no interaction with urobilinogen and/or bilirubin.

Methods for manufacturing a device according to this invention are known in the art. Generally, a first solution containing boric acid and polyvinylpyrrolidone is deposited onto a substrate, such as a filter paper. Then a second solution containing a thiazole ester of the invention and a diazonium salt, such as 2-methoxy-4-morpholinobenzene diazonium chloride, zinc chloride double salt, is deposited onto the substrate. Both solutions deposited onto the substrate may be free of a salt known in the art to have an accelerating action as described above.

To prepare a thiazole ester of the invention, a thiazolone derivative and an alanine or polyalanine derivative may be used as starting materials. Thiazolones may be synthesized by reacting carboxymethyl thiobenzimidate hydrobromide and pyridine.

As illustrated in the following scheme, the synthesis of a thiazole ester of the invention includes the reaction of a thiazolone derivative of the general formula (2), and an amino acid chloride of the general formula (3).

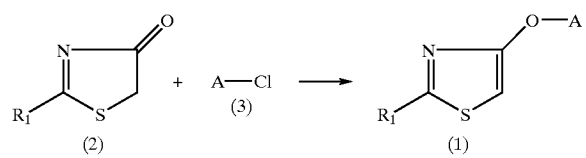

Each starting material is dissolved in solvent, and the resulting solutions are cooled and mixed slowly. This reaction mixture is stirred and then allowed to stand at room temperature for several hours. The reaction mixture is then washed, dried, filtered, and concentrated under reduced pressure. The solid, so formed, is dissolved in acetone and hexane is added. To remove any resulting hemisolid impurity, the reaction mixture is allowed to stand at low temperature for about 1 hour. Another portion of hexane is added to the residue and the mixture is refrigerated for 10 hours. The desired product is then filtered and dried.

Thiazolone derivatives tend to be highly reactive, resulting in dimerization or multimerization even during recrystallization. This may lead to poor yield. Thus, for the current invention, pure substances are isolated from the final product of the synthesis of the thiazole ester without purifying thiazolone of the general formula (2). This method of synthesis enhances the yield of the derivatives of the invention.

In contrast to this, the aforementioned indole or pyrrole derivatives have some recognized disadvantages. Many side reactions occur in the process of manufacturing their intermediates. Moreover, the reaction mechanism is very complicated and the yield for indole and pyrrole derivatives proves to be poor. But the synthesis of the thiazole esters of this invention allows for larger amounts of final product to be produced by a general method within a relatively short period of time. Moreover, because the method of synthesizing the thiazole esters of the invention is relatively simple and general, mass-scale production is more practical.

Methods of the invention include detecting the presence of leukocytes in urine. To detect the presence of leukocytes in urine, a urine sample is contacted with a thiazole ester of the invention and a diazonium salt in the presence of an accelerator. If leukocytes are present, then a reaction between thiazolyl and the salt produces an azo dye having a violet color.

Typically such a method is directed to contacting a urine sample with a substrate, for example, filter paper, that has a first solution of boric acid and polyvinyl pyrrolidone deposited thereon and then a second solution of a thiazole ester of formula I or II; a diazonium salt; and an accelerator deposited thereon. This method may be carried out free of an accelerating salt. When a urine sample containing leukocytes contacts such a substrate, then a violet color, which appears on the substrate, is observed.

WORKING EXAMPLES

This invention will be further characterized by the following examples. These examples are not meant to limit the scope of the invention, which has been fully set forth in the foregoing description. Variations within the scope of the invention are apparent to those skilled in the art.

Example 1

N-(p-Toluenesulfonyl)-alanine $$CH_3-C_6H_4-S(=O)_2-NH-CH(CH_3)-COOH$$

To synthesize a starting material containing a blocked N-alanine, N-(p-toluenesulfonyl)-alanine is first synthesized.

50.0 g of p-toluenesulfonyl chloride was added to 100 ml of 90° C. toluene with stirring. The p-toluenesulfonyl chloride solution in toluene was slowly added to 25.0 g of L-alanine dissolved in 500 ml of 1N NaOH cooled to 5° C. and stirred for 24 hours. The resulting aqueous layer is separated and cooled to below 5° C. and with the addition of concentrated hydrochloric acid, pH was adjusted to 1.5. After standing in the refrigerator for 3 to 4 hours, the white solid crystals, so formed, were filtered, twice washed with water, and dried.

Example 2

N-Tosyl-L-alanyl Chloride $$CH_3-C_6H_4-S(=O)_2-NH-CH(CH_3)-C(=O)-Cl$$

The blocked starting material is next produced by reacting N-(p-toluenesulfonyl)-alanine and oxalyl chloride.

30.0 g of N-(p-toluenesulfonyl)-alanine and 6 to 7 drops of DMF (dimethylformamide) were dissolved in 100 ml of dichloromethane and 5 ml of oxalyl chloride was added dropwise. After stirring for 3 hours at room temperature the reaction mixture was evaporated down to a residue which was dissolved in 100 ml of dichloromethane. The dichloromethane was again evaporated and the resulting residue dissolved in 50 ml of dichloromethane followed by the addition of 100 ml hexane. After standing in the refrigerator overnight the crystals, so formed, were filtered and dried.

Example 3

2-(4-Pyridyl)-4-thiazol

HCl gas is bubbled through a solution of 10 g of 4-cyanopyridine and 50 g of mercaptoacetic acid in approximately 20 ml of ether and 30 ml of chloroform for 24 hours. During the reaction 30 ml of ether and 50 ml of chloroform are added. The crystallized product, so formed, is filtered, washed with a solvent system of 1:1 ether and chloroform, and dried.

Example 4

2-(2-Thienyl)-4-thiazol

HCl gas was bubbled through a solution of 10 g of 3-thiophenecarbonitrile and 35 g of mercaptoacetic acid in approximately 50 ml of ether for 24 hours. The crystallized product, so formed, was filtered, washed with 200 ml ether, and dried.

Example 5

2-(1-Naphthyl)-4-thiazol

HCl gas was bubbled through a solution of 25 g of 1-naphthonitrile and 25 g of mercaptoacetic acid in approximately 150 ml chloroform for 24 hours. The crystallized product, so formed, was filtered, washed with 200 ml chloroform, and dried.

Example 6

2-(1,2-Dimethyl-4-pyrrolyl)-4-thiazol

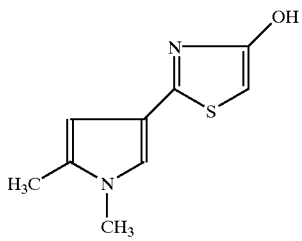

HCl gas was bubbled through a solution of 5 g of 1,5-dimethyl-2-pyrrolecarbonitrile and 5 g of mercaptoacetic acid in approximately 50 ml of ether/chloroform (1:1) for 24 hours. The crystallized product, so formed, was filtered, washed with 100 ml ether/chloroform (1:1), and dried.

Example 7

2-(3-Indolyl)-4-thiazol

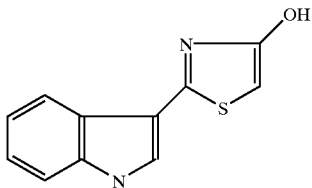

HCl gas is bubbled through a solution of 5 g of 3-cyanoindole and 5 g of mercaptoacetic acid in approximately 50 ml of ether/chloroform (1:1) for 24 hours. The crystallized product, so formed, is filtered, washed with 100 ml ether/chloroform (1:1), and dried.

Example 8

2-(2-Furyl)-4-thiazol

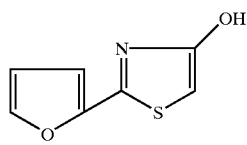

HCl gas was bubbled through a solution of 5 g of 2-furonitrile and 5 g of mercaptoacetic acid in approximately 50 ml of ether/chloroform (1:1) for 24 hours. The crystallized product, so formed, was filtered, washed with 100 ml ether/chloroform (1:1), and dried.

Example 9

2-($\beta$-Styryl)-4-thiazol

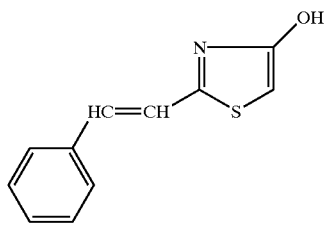

HCl gas was bubbled through a solution of 25 g of cinnamonitrile and 25 g of mercaptoacetic acid in approximately 150 ml of ether/chloroform (1:1) for 24 hours. The crystallized product, so formed, was filtered, washed with 200 ml ether/chloroform (1:1), and dried.

Example 10

2-(4-Pyridyl)-4-(N-tosyl-L-alanyloxy) thiazol

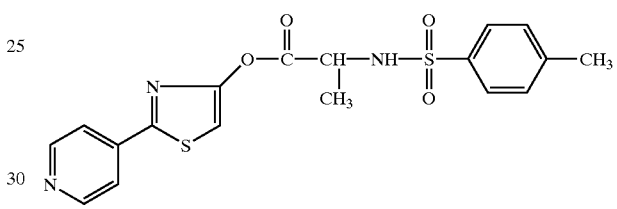

5.0 g of 2-(4-pyridyl)-4-thiazol is dissolved in a cosolvent of 100 ml of dichloromethane and 10 ml pyridine and cooled to 5° C. A solution of 15.0 g of N-tosyl-L-alanyl chloride in 50 ml dichloromethane is then added dropwise to the above mixture. The reaction solution is stirred at room temperature or until the reaction is complete. The solution is washed with 1N hydrochloric acid, water, saturated sodium bicarbonate, and a saturated sodium chloride solution in that order; dried over magnesium sulfonate; filtered; and concentrated under reduced pressure. The residue, so formed, is dissolved in 100 ml of acteone and 100 ml of hexane is added. After standing in the refrigerator for 1 hour, dark semisolid impurities are decanted off and the remaining solvent evaporated. The amorphous solid, so formed, is dissolved in a minimum of ethylacetate, the resulting solution is then applied to a silica column and eluted with a 2:1 ethylacetate/hexane solvent system. Fractions containing the desired product are collected, the solvent is evaporated, and the resulting residue is dissolved in 20 ml of acetone followed by the addition of 50 ml hexane. After standing in the refrigerator the product, so formed, is filtered and dried.

Example 11

2-(2-Thienyl)-4-(N-tosyl-L-alanyloxy) thiazol

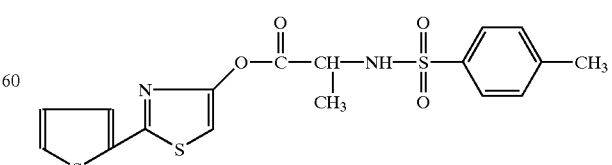

5.0 g of 2-(3-thienyl)-4-thiazol was dissolved in a cosolvent of 100 ml of dichloromethane and 10 ml pyridine and cooled to 5° C. A solution of 15.0 g of N-tosyl-L-alanyl chloride in 50 ml dichloromethane was then added dropwise to the above mixture. The reaction solution was stirred at room temperature until the reaction was complete. The solution was washed with 1N hydrochloric acid, water, saturated sodium bicarbonate, and a saturated sodium chloride solution in that order; dried over magnesium sulfonate; filtered; and concentrated under reduced pressure. The residue, so formed, was dissolved in 100 ml of acteone and 100 ml of hexane was added. After standing in the refrigerator for 1 hour, dark semisolid impurities were decanted off and the remaining solvent evaporated. The amorphous solid, so formed, was dissolved in a minimum of ethylacetate, the resulting solution applied to a silica column and eluted with a 2:1 ethylacetate/hexane solvent system. Fractions containing the desired product were collected, the solvent was evaporated, and the resulting residue was dissolved in 20 ml of acetone followed by the addition of 50 ml hexane. After standing in the refrigerator the product so formed, was filtered and dried.

The product was identified by a proton NMR analysis. A sample of the product was dissolved in acetone-$d_6$ (19 mg/0.7 ml) and a proton spectrum was collected following AMRI SOP INS-041 using a Bruker® 300 MHz NMR Spectrometer (Bruker-Physik AG, Germany).

The identity of the product was further confirmed by infrared spectral analysis by first mixing 263 mg of potassium bromide with 1.7 mg of the product and then grinding them in a Wig L Bug® (Crescent Dental Manufacturing Co., Illinois). The ground mixture was pressed into a disk and an infrared spectrum was collected by a Spectrum 1000 IR Spectrometer following AMRI SOP INS-026. The sample was scanned between 4000 and 400 $cm^{-1}$.

Example 12

2-(1-Naphthyl)-4-(N-tosyl-L-alanyloxy) thiazol

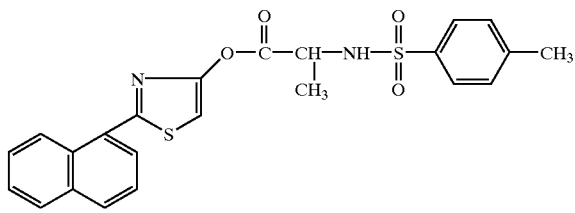

5.0 g of 2-(1-naphthyl)-4-thiazol is dissolved in a cosolvent of 100 ml of dichloromethane and 10 ml pyridine and cooled to 5° C. A solution of 15.0 g of N-tosyl-L-alanyl chloride in 50 ml dichloromethane is then added dropwise to the above mixture. The reaction solution is stirred at room temperature until the reaction is complete. The solution is washed with 1N hydrochloric acid, water, saturated sodium bicarbonate, and a saturated sodium chloride solution in that order; dried over magnesium sulfonate; filtered; and concentrated under reduced pressure. The residue, so formed, is dissolved in 100 ml of acteone and 100 ml of hexane is added. After standing in the refrigerator for 1 hour, dark semisolid impurities are decanted off and the remaining solvent evaporated. The amorphous solid, so formed, is dissolved in a minimum of ethylacetate, the resulting solution is then applied to a silica column and eluted with a 2:1 ethylacetate/hexane solvent system. Fractions containing the desired product are collected, the solvent is evaporated, and the resulting residue is dissolved in 20 ml of acetone followed by the addition of 50 ml hexane. After standing in the refrigerator the product, so formed, is filtered and dried.

Example 13

2-(1,2-Dimethyl-4-pyrrolyl)-4-(N-tosyl-L-alanyloxy) thiazol

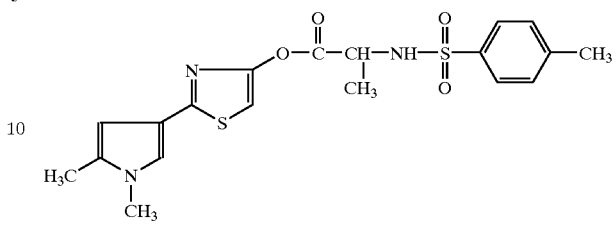

5.0 g of 2-(1,2-dimethyl-4-pyrrolyl)-4-thiazol is dissolved in a cosolvent of 100 ml of dichloromethane and 10 ml pyridine and cooled to 5° C. A solution of 15.0 g of N-tosyl-L-alanyl chloride in 50 ml dichloromethane is then added dropwise to the above mixture. The reaction solution is stirred at room temperature or until the reaction is complete. The solution is washed with 1N hydrochloric acid, water, saturated sodium bicarbonate, and a saturated sodium chloride solution in that order; dried over magnesium sulfonate; filtered; and concentrated under reduced pressure. The residue, so formed, is dissolved in 100 ml of acteone and 100 ml of hexane is added. After standing in the refrigerator for 1 hour, dark semisolid impurities are decanted off and the remaining solvent evaporated. The amorphous solid, so formed, is dissolved in a minimum of ethylacetate, the resulting solution is then applied to a silica column and eluted with a 2:1 ethylacetate/hexane solvent system. Fractions containing the desired product are collected, the solvent is evaporated, and the resulting residue is dissolved in 20 ml of acetone followed by the addition of 50 ml hexane. After standing in the refrigerator the product, so formed, is filtered and dried.

Example 14

2-(3-Indolyl)-4-(N-tosyl-L-alanyloxy)thiazol

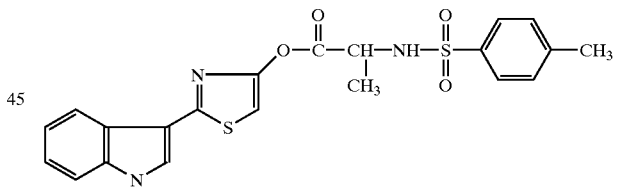

5.0 g of 2-(3-indolyl)-4-thiazol is dissolved in a cosolvent of 100 ml of dichloromethane and 10 ml pyridine and cooled to 5° C. A solution of 15.0 g of N-tosyl-L-alanyl chloride in 50 ml dichloromethane is then added dropwise to the above mixture. The reaction solution is stirred at room temperature until the reaction is complete. The solution is washed with 1N hydrochloric acid, water, saturated sodium bicarbonate, and a saturated sodium chloride solution in that order; dried over magnesium sulfonate; filtered; and concentrated under reduced pressure. The residue, so formed, is dissolved in 100 ml of acteone and 100 ml of hexane is added. After standing in the refrigerator for 1 hour, dark semisolid impurities are decanted off and the remaining solvent evaporated. The amorphous solid, so formed, is dissolved in a minimum of ethylacetate, the resulting solution is then applied to a silica column and eluted with a 2:1 ethylacetate/hexane solvent system. Fractions containing the desired product are collected, the solvent is evaporated, and the resulting residue is dissolved in 20 ml of acetone followed by the addition of 50 ml hexane. After standing in the refrigerator the product, so formed, is filtered and dried.

Example 15

2-(2-Furyl)-4-(N-tosyl-L-alanyloxy) thiazol

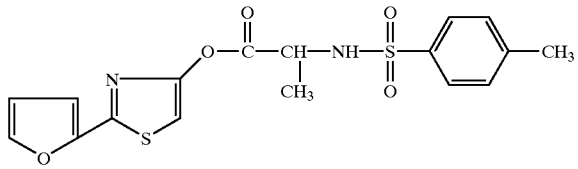

5.0 g of 2-(2-furyl)-4-thiazol is dissolved in a cosolvent of 100 ml of dichloromethane and 10 ml pyridine and cooled to 5° C. A solution of 15.0 g of N-tosyl-L-alanyl chloride in 50 ml dichloromethane is then added dropwise to the above mixture. The reaction solution is stirred at room temperature until the reaction is complete. The solution is washed with 1N hydrochloric acid, water, saturated sodium bicarbonate, and a saturated sodium chloride solution in that order; dried over magnesium sulfonate; filtered; and concentrated under reduced pressure. The residue, so formed, is dissolved in 100 ml of acteone and 100 ml of hexane is added. After standing in the refrigerator for 1 hour, dark semisolid impurities are decanted off and the remaining solvent evaporated. The amorphous solid, so formed, is dissolved in a minimum of ethylacetate, the resulting solution is then applied to a silica column and eluted with a 2:1 ethylacetate/hexane solvent system. Fractions containing the desired product are collected, the solvent is evaporated, and the resulting residue is dissolved in 20 ml of acetone followed by the addition of 50 ml hexane. After standing in the refrigerator the product, so formed, is filtered and dried.

Example 16

2-(β-Styryl)-4-(N-tosyl-L-alanyloxy) thiazol

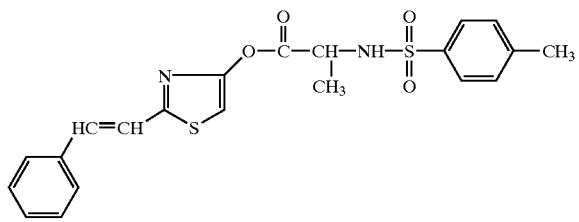

5.0 g of 2-(β-stryl)-4-thiazol was dissolved in a cosolvent of 100 ml of dichloromethane and 10 ml pyridine and cooled to 5° C. A solution of 15.0 g of N-tosyl-L-alanyl chloride in 50 ml dichloromethane was then added dropwise to the above mixture. The reaction solution was stirred at room temperature until the reaction was complete. The solution was washed with 1N hydrochloric acid, water, saturated sodium bicarbonate, and a saturated sodium chloride solution in that order; dried over magnesium sulfonate; filtered; and concentrated under reduced pressure. The residue, so formed, was dissolved in 100 ml of acteone and 100 ml of hexane was added. After standing in the refrigerator for 1 hour, dark semisolid impurities were decanted off and the remaining solvent evaporated. The amorphous solid, so formed, was dissolved in a minimum of ethylacetate, the resulting solution applied to a silica column and eluted with a 2:1 ethylacetate/hexane solvent system. Fractions containing the desired product were collected, the solvent was evaporated, and the resulting residue was dissolved in 20 ml of acetone followed by the addition of 50 ml hexane. After standing in the refrigerator the product, so formed, was filtered and dried.

Example 17

Preparation of a Leukocyte Diagnostic Device

To detect the presence of leukocytes in urine, a test strip containing a compound of the invention was prepared. A small type of testing paper in a regular square was attached to the end of a polystyrene strip, sedimented, and dried with the following two mixing solutions successively. The first solution (100 ml of aqueous solution) contained 5% (w/v) boric acid (pH 7.7) and 2% (w/v) polyvinyl pyrrolidone (K-10). The sedimented paper was dried by heating at 60° C. for 10 minutes. A second solution (100 ml of acetone) contained 0.06% (w/v) of 2-(2-thienyl)-4-(N-tosyl-L-alanyloxy) thiazol or 2-(β-styryl)-4-(N-tosyl-L-alanyloxy) thiazol; 0.05% (w/v) 2-methoxy-4-morpholinobenzene diazonium chloride zinc chloride disalts and 1.0% (w/v) n-decanol. The sedimented paper was dried by heating at 50° C. for 5 minutes.

Successful leukocyte assays (i.e., the assays were useful for correctly identifying the presence of leukocytes in urine) were carried out using a diagnostic device that contained each one of the thiazole esters listed in this Example.

Each assay was conducted by contacting a test strip (manufactured as described above) with a urine sample. When the urine sample contained leukocytes, the test strip showed the appearance of a violet color. The initial tint of violet color appeared within about 10 seconds and gradually darkened until the reaction was complete, which was about 1 minute. The completed reaction showed a degree of color change that was suitable not only for identifying whether leukocytes were present in the urine sample but also for semiquantitatively determining the concentration of the leukocytes present.

Example 18

Preparation of a Leukocyte Diagnostic Device

To detect the presence of leukocytes in urine, a test strip containing a composition of the invention is prepared. A small type of testing paper in a regular square is attached to the end of a polystyrene strip, sedimented, and dried with the following two mixing solutions successively. The first solution (100 ml of aqueous solution) contains 5% (w/v) boric acid (pH 7.7) and 2% (w/v) polyvinyl pyrrolidone (K-10). The sedimented paper is dried by heating at 60° C. for 10 minutes. A second solution (100 ml of acetone) contains 0.06% (w/v) of 2-(4-pyridyl)-4-(N-tosyl-L-alanyloxy) thiazol; 2-(1-naphthyl)-4-(N-tosyl-L-alanyloxy) thiazole; 2-(1, 2-dimethyl-4-pyrrolyl)-4-(N-tosyl-L-alanyloxy) thiazol; 2-(2-furyl)-4-(N-tosyl-L-alanyloxy) thiazol; or 2-(3-indolyl)-4-(N-tosyl-L-alanyloxy) thiazol; 0.05% (w/v) 2-methoxy-4-morpholinobenzene diazonium chloride zinc chloride disalts and 1.0% (w/v) n-decanol. The sedimented paper is dried by heating at 50° C. for 5 minutes.

Each assay is conducted by contacting a test strip (manufactured as described above) with a urine sample. When the urine sample contains leukocytes, the test strip shows the appearance of a violet color. The initial tint of violet color appears within about 10 seconds and gradually darkens until the reaction is complete, which is about 1 minute. The completed reaction shows a degree of color change that is suitable not only for identifying whether leukocytes are present in the urine sample but also for semiquantitatively determining the concentration of the leukocytes.

The above specification, examples, and data provide a complete description of the manufacture and the use of the many methods, compounds, compositions, and devices of the invention. Since many embodiments of the invention can be made without departing from the spirit and the scope of the invention, the invention resides in the claims hereinafter appended.

What is claimed is:

1. A diagnostic device for detecting leukocytes in urine, comprising:

an inert carrier having deposited thereon a compound of the formula:

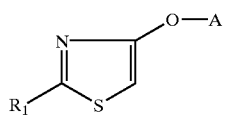

(I)

or a salt or solvated salt thereof, wherein

A is an N-blocked amino acid residue or N-blocked peptide chain; and

R₁ is unsubstituted or substituted heteroaryl; alkenyl substituted with unsubstituted or substituted aryl; or alkenyl substituted with unsubstituted or substituted heteroaryl.

2. The device of claim 1, wherein the compound has R₁ that is heteroaryl substituted with alkyl, alkoxy, alkenyl, amino, acyl, halo, nitro, cyano, hydroxy, or —SO₃H.

3. The device of claim 1, wherein the compound has R₁ that is unsubstituted or substituted heteroaryl that is selected from the group consisting of a 5-membered ring and a 6-membered ring.

4. The device of claim 1, wherein the compound has R₁ that is unsubstituted or substituted heteroaryl selected from the group consisting of a nitrogen-containing ring, an oxygen-containing ring, and a sulfur-containing ring.

5. The device of claim 1, wherein the compound has R₁ that is alkenyl selected from the group consisting of ethenyl, propenyl, and butenyl, the alkenyl being substituted with unsubstituted or substituted aryl or unsubstituted or substituted heteroaryl.

6. The device of claim 1, wherein the compound has R₁ that is alkenyl substituted with aryl that is unsubstituted phenyl or substituted phenyl.

7. The device of claim 6, wherein the phenyl is substituted with alkyl, alkenyl, alkoxy, amino, acyl, halo, nitro, cyano, hydroxy, or —SO₃H.

8. The device of claim 1, wherein the compound has R₁ that is alkenyl substituted with heteroaryl, wherein the heteroaryl is substituted with alkyl, alkoxy, alkenyl, amino, acyl, halo, nitro, cyano, hydroxy, or —SO₃H.

9. The device of claim 1, wherein the compound has R₁ that is alkenyl substituted with heteroaryl that is selected from the group consisting of a 5-membered ring and a 6-membered ring.

10. The device of claim 1, wherein the compound has R₁ that is alkenyl substituted with heteroaryl that is selected from the group consisting of a nitrogen-containing ring, an oxygen-containing ring, and a sulfur-containing ring.

11. The device of claim 1, wherein the compound has R₁ that is heteroaryl substituted with alkyl or alkoxy.

12. The device of claim 1, wherein the compound is of the formula

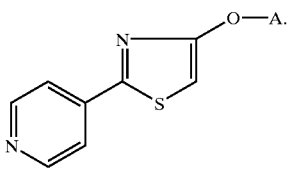

13. The device of claim 1, wherein the compound is of the formula:

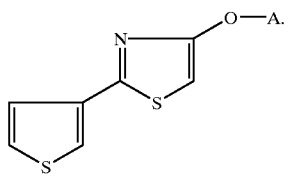

14. The device of claim 1, wherein the compound is of the formula:

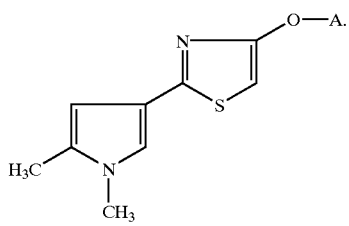

15. The device of claim 1, wherein the compound is of the formula:

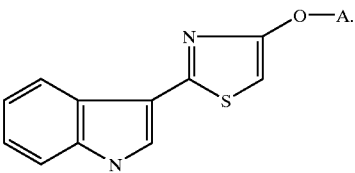

16. The device of claim 1, wherein the compound is of the formula:

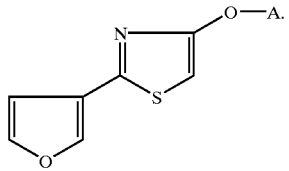

17. The device of claim 1, wherein the compound is of the formula:

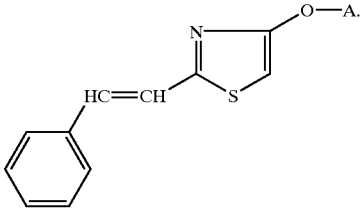

18. The device of claim 1, wherein the compound has A that is N-blocked alanine or N-blocked polyalanine.

19. The device of claim 1, wherein the inert carrier has a diazonium salt deposited thereon.

20. The device of claim 19, wherein the diazonium salt is selected from the group consisting of 1-diazo-8-naphtol-3,6-disulfonic acid, chloride, zinc chloride double salt; 6-diazo-1-naphtol-3-sulfonic acid, chloride double salt; and 2-methoxy-4-morpholinobenzene diazonium chloride, zinc chloride double salt.

21. The device of claim 1, wherein the inert carrier is a filter paper.

22. The device of claim 1, wherein the device is free of accelerating salt.

23. A diagnostic device for detecting the presence of leukocytes in urine, comprising:
an inert carrier having deposited thereon a compound of the formula:

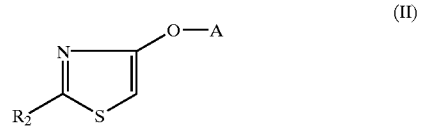

(II)

or a salt or solvated salt thereof, wherein
A is an N-blocked amino acid residue or N-blocked peptide chain; and
$R_2$ is unsubstituted or substituted fused hydrocarbyl rings in which at least one ring is aromatic.

24. The device of claim 23, wherein the compound has $R_2$ selected from the group consisting of naphthyl, tetrahydronaphthyl, and anthryl.

25. The device of claim 23, wherein the fused hydrocarbyl rings are substituted on at least one ring with alkyl, alkoxy, alkenyl, amino, acyl, halo, nitro, cyano, hydroxy, or $-SO_3H$.

26. The device of claim 23, wherein the fused hydrocarbyl rings contain at least one ring selected from the group consisting of a 5-membered ring and a 6-membered ring.

27. The device of claim 23, wherein the fused hydrocarbyl rings are substituted on at least one ring with alkyl or alkoxy.

28. The device of claim 23, wherein the compound is of the formula:

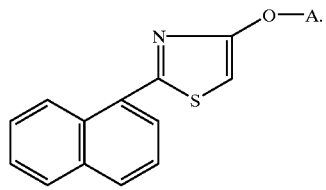

29. The device of claim 23, wherein the compound has A that is N-blocked alanine or N-blocked polyalanine.

30. The device of claim 23, wherein the inert carrier has a diazonium salt deposited thereon.

31. The device of claim 30, wherein the diazonium salt is selected from the group consisting of 1-diazo-8-naphtol-3,6-disulfonic acid, chloride, zinc chloride double salt; 6-diazo-1-naphtol-3-sulfonic acid, chloride double salt; and 2-methoxy-4-morpholinobenzene diazonium chloride, zinc chloride double salt.

32. The device of claim 23, wherein the inert carrier is a filter paper.

33. The device of clam 23, wherein the device is free of accelerating salt.

34. A method of detecting the presence of leukocytes in urine, comprising:
contacting a urine sample with a diazonium salt and a compound of the formula:

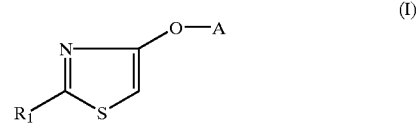

(I)

or a salt or solvated salt thereof, wherein
A is an N-blocked amino acid residue or N-blocked peptide chain; and
$R_1$ is unsubstituted or substituted heteroaryl; alkenyl substituted with unsubstituted or substituted aryl; or alkenyl substituted with unsubstituted or substituted heteroaryl.

35. The method of claim 34, wherein the diazonium salt is selected from the group consisting of 1-diazo-8-naphtol-3,6-disulfonic acid, chloride, zinc chloride double salt; 6-diazo-1-naphtol-3-sulfonic acid, chloride double salt; and 2-methoxy-4-morpholinobenzene diazonium chloride, zinc chloride double salt.

36. The method of claim 34, wherein the method is free of accelerating salt.

37. The method of claim 34, wherein the compound has $R_1$ that is heteroaryl substituted with alkyl, alkoxy, alkenyl, amino, acyl, halo, nitro, cyano, hydroxy, or $-SO_3H$.

38. The method of claim 34, wherein the compound has $R_1$ that is unsubstituted or substituted heteroaryl selected from the group consisting of a 5-membered ring and a 6-membered ring.

39. The method of claim 34, wherein the compound has $R_1$ that is unsubstituted or substituted heteroaryl selected from the group consisting of a nitrogen-containing ring, oxygen-containing ring, and a sulfur-containing ring.

40. The method of claim 34, wherein the compound has $R_1$ that is alkenyl selected from the group consisting of ethenyl, propenyl, and butenyl, the alkenyl being substituted with unsubstituted or substituted aryl or unsubstituted or substituted heteroaryl.

41. The method of claim 34, wherein the compound has $R_1$ that is alkenyl substituted with aryl that is unsubstituted phenyl or substituted phenyl.

42. The method of claim 41, wherein the phenyl is substituted with alkyl, alkenyl, alkoxy, amino, acyl, halo, nitro, cyano, hydroxy, or $-SO_3H$.

43. The method of claim 34, wherein the compound has $R_1$ that is alkenyl substituted with heteroaryl, wherein the heteroaryl is substituted with alkyl, alkoxy, alkenyl, amino, acyl, halo, nitro, cyano, hydroxy, or $-SO_3H$.

44. The method of claim 34, wherein the compound has $R_1$ that is alkenyl substituted with heteroaryl that is selected from the group consisting of a 5-membered ring and a 6-membered ring.

45. The method of claim 34, wherein the compound has $R_1$ that is alkenyl substituted with heteroaryl selected from the group consisting of a nitrogen-containing ring, an oxygen-containing ring, and a sulfur-containing ring.

46. The method of claim 34, wherein the compound has $R_1$ that is heteroaryl substituted with alkyl or alkoxy.

47. The method of claim 34, wherein the compound is of the formula:

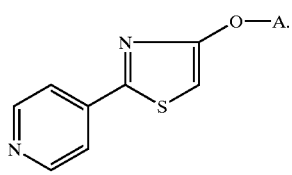

48. The method of claim 34, wherein the compound is of the formula:

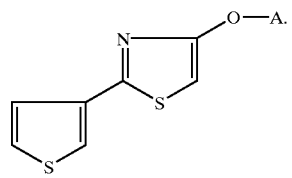

49. The method of claim 34, wherein the compound is of the formula:

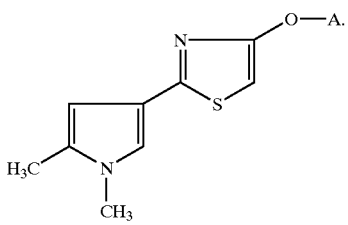

50. The method of claim 34, wherein the compound is of the formula:

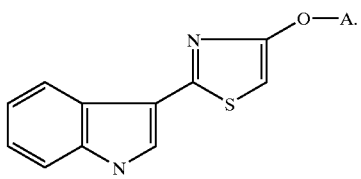

51. The method of claim 34, wherein the compound is of the formula:

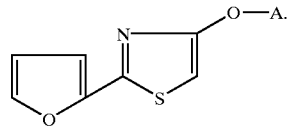

52. The method of claim 34, wherein the compound is of the formula:

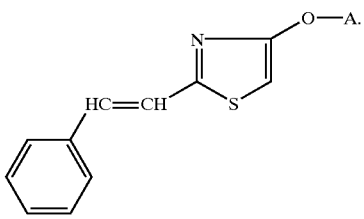

53. The method of claim 34, wherein the compound has A that is N-blocked alanine or N-blocked polyalanine.

54. A method for detecting the presence of leukocytes in urine, comprising:
  contacting a urine sample with a diazonium salt and a compound of the formula:

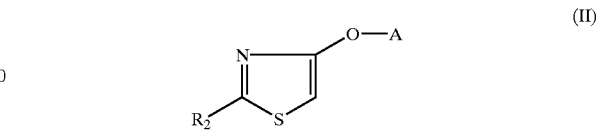

(II)

or a salt or solvated salt thereof, wherein
  A is an N-blocked amino acid residue or N-blocked peptide chain; and
  $R_2$ is unsubstituted or substituted fused hydrocarbyl rings in which at least one ring is aromatic.

55. The method of claim 54, wherein the diazonium salt is selected from the group consisting of 1-diazo-8-naphtol-3,6-disulfonic acid, chloride, zinc chloride double salt; 6-diazo-1-naphtol-3-sulfonic acid, chloride double salt; and 2-methoxy-4-morpholinobenzene diazonium chloride, zinc chloride double salt.

56. The method of claim 54, wherein the method is free of accelerating salt.

57. The method of claim 54, wherein the compound has $R_2$ selected from the group consisting of naphthyl, tetrahydronaphthyl, and anthryl.

58. The method of claim 54, wherein the fused hydrocarbyl rings are substituted on at least one ring with alkyl, alkoxy, alkenyl, amino, acyl, halo, nitro, cyano, hydroxy, or —$SO_3H$.

59. The method of claim 54, wherein the fused hydrocarbyl rings contain at least one ring selected from the group consisting of a 5-membered ring and a 6-membered ring.

60. The method of claim 54, wherein the fused hydrocarbyl rings are substituted on at least one ring with alkyl or alkoxy.

61. The method of claim 54, wherein the compound is of the formula:

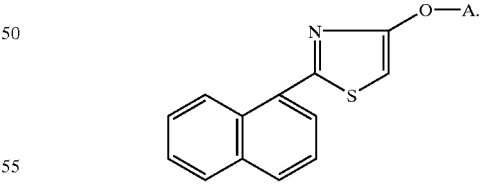

62. The method of claim 54, wherein the compound has A that is N-blocked alanine or N-blocked polyalanine.

* * * * *